United States Patent [19]

Della Bella et al.

[11] 4,276,299

[45] Jun. 30, 1981

[54] 1-(3-BROMO-ISOXAZOL-5-YL)-2-TERT.-BUTYLAMINOETHANOL

[75] Inventors: Davide Della Bella; Dario Chiarino, both of Milan, Italy

[73] Assignee: Zambon S.p.A., Milan, Italy

[21] Appl. No.: 104,740

[22] Filed: Dec. 18, 1979

[30] Foreign Application Priority Data

Dec. 22, 1978 [IT] Italy ................................ 31198 A/78

[51] Int. Cl.³ ..................... A61K 31/42; C07D 261/06
[52] U.S. Cl. ..................................... 424/272; 548/247
[58] Field of Search ........................ 548/247; 424/272

[56] References Cited

U.S. PATENT DOCUMENTS 3,321,475  5/1967  Kano et al. ......................... 548/247

*Primary Examiner*—Anton H. Sutto
*Attorney, Agent, or Firm*—Stevens, Davis, Miller & Mosher

[57] ABSTRACT

A new isoxazole derivative and the preparation thereof are disclosed. 1-(3-Bromo-isoxazol-5-yl)-2-ter.-butylaminoethanol endowed with therapeutic activity, in particular bronchodilating action is disclosed, as well as a method for preparing same from 3-bromo-5-isoxazolecarboxylic acid. New intermediate compounds as well as pharmaceutical compositions containing the novel isoxazole derivative are also disclosed.

4 Claims, No Drawings

1-(3-BROMO-ISOXAZOL-5-YL)-2-TERT.BUTYLAMINOETHANOL

The present invention relates to a new isoxazole derivative showing therapeutic activity, to the salts thereof, to the pharmaceutical compositions containing the new isoxazole derivatives, as well as to its method of preparation.

More particularly, the present invention provides 1-(3-bromo-isoxazol-5-yl)-2-ter.butylaminoethanol (which hereinbelow will be for brevity indicated as Z 1170) of the formula:

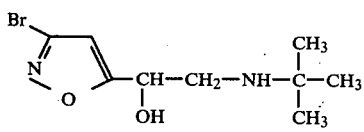

Furthermore, the present invention provides pharmaceutically acceptable salts of Z 1170 with both organic and inorganic acids such as for instance the hydrochloride, the neutral sulphate, the acid maleate.

A further object of the present invention is to provide pharmaceutical compositions containing Z 1170 together with suitable carriers.

Other objects of the invention will become clear from the description.

Z 1170 can be prepared from 3-bromo-5-isoxazolecarboxylic acid which in turn is obtained according to processes described in the literature [J. Thiele, H. Landers, Ann. 369, 300 (1909); R. Fusco et al, Ist. Lombardo Sci., pt. I, Classe Sci. Mat. e Nat. 94A, 729–740 (1960); P. Bravo et al, Gazz. Chim. Ital. 91, 47–64 (1961)].

The 3-bromo-5-isoxazolecarboxylic acid is treated with a chlorinating agent thus giving the chloride of the 3-bromo-5-isoxazolecarboxylic acid.

The 3-bromo-5-isoxazolecarboxylic acid chloride is transformed into the 3-bromo-5-acetyl-isoxazole (II) by reaction with suitable nucleophile alkylating agents such as for instance the alkoxymagnesium malonic ester and the alkali malonic mono- and di-esters and, preferably, with diethylethoxy magnesium malonate, followed by hydrolysis and decarboxylation.

The 1-(3-bromo-isoxazol-5-yl)-2-bromoethanol (IV) is obtained by bromination of the compound (II) and reduction of the 3-bromo-5-bromacetyl-isoxazole (III).

From (IV) Z 1170 is obtained by treatment with ter. butylamine.

Alternatively, the compound (IV) can be transformed into the 2-(3-bromo-isoxazol-5-yl)-oxirane (V) by treatment with sodium hydride. By reaction with ter.butylamine the compound (V) is converted to Z 1170.

Alternatively, the 2-(3-bromo-isoxazol-5-yl)-oxirane (V) can be prepared by reacting the dibromoformoxime with ethinyloxirane.

The intermediate compounds (II), (III), (IV), and (V) are not described in literature.

It is therefore a further object of the present invention to provide the intermediate compounds (II), (III), (IV), and (V).

Z 1170 is a new $\beta_2$-specific sympathomimetic drug which has been shown to be effective and long-lasting bronchodilating agent in animals, active by the oral and parenteral routes, with greater selectivity for bronchial smooth muscle than for cardiac muscle.

Many experiments both in vitro and in vivo have been carried out in order to characterize the new isoxazole derivative of the present invention from the pharmacological point of view.

By using the guinea pig tracheal test [Castillo J. C., De Beer E. J., J. Pharmacol. Exp. Ther., 90, 104 (1947)] as well as the guinea pig right atria test [Kaiser C. el al, J. Med. Chem. 17, 49 (1974)] isolated in vitro, the isoxazole derivative of this invention shows a selective agonist action on the $\beta_2$-adrenergic tracheal receptor (relative potency T=0.095) whereas the agonist action on the $\beta_1$adrenergic receptor of the right atrium appears to be clearly lower (relative potency A=0.002). Therefore, the ratio T/A is very favorable: 45.5.

In the tests in vivo carried out on the guinea pig narcotized with urethan, it was observed that a dose of 100 μg/kg of Z 1170 introvenously administered resulted in an over 80% reduction of the bronchocostriction effect from histamine. After 150 minutes the antagonistic effect was still over 50%.

The Z 1170 derivative orally administered at the dose of 1 mg/kg protracts for more than double the survival time for exposure of the animal at aerosol both with 1% solution of histamine and 1% solution of serotonin.

The protection is still clearly detectable 6 hours after the administration. The protection from Z 1170 can be observed also in the event that the administration is carried out by aerosol using a 0.5% solution, 15 minutes before the aerosol with a solution of bronchocostricting drugs. Also in this case the survival time to the exposure of aerosol of bronchocostricting drugs appears to be more than double. The influence of Z 1170 on the muscular $\beta_2$-adrenergic receptors, and consequently the trembling action, has been investigated by tests in vivo, in the cat, using the soleus muscle preparation [Bowman W. C., Nott M. W., Br. J. Pharmacol. 38, 37, (1970)].

The experimental results have shown that, as far as the cat soleus muscle test is concerned, the Z 1170 is about a hundred times less active than isoproterenol.

The Z 1170 is endowed, as to the different administration ways and in the different animal species, with a particularly favorable tolerance.

The $LD_{50}$ values obtained are listed in the following table:

| Species | Administration | $LD_{50}$ mg/kg | (Limits for P = 0.05) |
|---|---|---|---|
| Mouse | os | 770 | (707–840) |
|  | i.p. | 230 | (209–254) |
|  | i.v. | 126 | (113–140) |
|  | (1 ml/100 g/60″) | (0.42 mols/kg) |  |
| Rat | os | >2000 |  |
|  | i.v. | 196 | (185–208) |
|  | (1 ml/100 g/60″) | (0.65 mols/kg) |  |

The compositions may contain the Z 1170 and the pharmaceutically acceptable acid addition salts thereof together with a pharmaceutically acceptable carrier or support.

This carrier or support may be an organic or inorganic inert material rendering the composition suitable for oral or parenteral administration.

The composition can be made up in a solid form or in a liquid form.

Z 1170 may be administered orally in form of tables of 0.5 mg to be dissolved in water for use. An example of formulation for tablets for oral administration is given hereinbelow:

| | |
|---|---|
| Z 1170 | 0.50 mg |
| sodium citrate (dibasic) | 82.00 mg |
| sodium bicarbonate | 26.30 mg |
| polyvinylpyrrolidone | 3.10 mg |
| sodium benzoate | 6.10 mg. |

Other possible administration routes for Z 1170 are the intravenous and the aerosol administration.

The following examples on the preparation of Z 1170 further illustrate the invention without limiting it in any way.

EXAMPLE 1

Preparation of the chloride of the 3-bromo-5-isoxazolecarboxylic acid. 5.10 g (70 millimols) of dimethylformamide were added to a mixture of 19.20 g (100 millimols) of 3-bromo-5-isoxazolecarboxylic acid and 160 ml of thionyl chloride. After refluxing for 20 minutes, the thionyl chloride was removed under vacuum and the residue was treated with 30 ml of carbon tetrachloride.

The mixture was filtered off and the residue was extracted with 2 portions each of 20 ml of carbon tetrachloride.

The thus obtained filtrate and extracts were combined and then evaporated under vacuum.

The residue was distilled off whereupon 17.0 g (81%) of the chloride of 3-bromo-5-isoxazolecarboxylic acid were obtained in the form of a colorless oil, boiling at 77°–78°/8 mm Hg. On standing the product gave crystals melting at 38° C. $^1$H NMR (CDCl$_3$): $\delta$7.17 (s, 1H, C=CH—C).

EXAMPLE 2

Preparation of 3-bromo-5-acetylisoxazole.

4.90 g (202 millimols) of magnesium were added to a solution of 30.9 g (193 millimols) of diethylmalonate, 14.00 g (300 millimols) of ethanol, and 0.9 ml of carbon tetrachloride in ether (176 ml).

The mixture was refluxed for 5 hours and then was filtered off; a solution of 36 g (175 millimols) of the chloride of the 3-bromo-5-isoxazolecarboxylic acid in ether (117 ml) was then added slowly, and under stirring, to the refluxing filtrate.

The reaction mixture was kept under reflux for a further 30 minutes, and after cooling down to room temperature, 351 ml of 2 M H$_2$SO$_4$ were added, the ether phase was separated, dried, and concentrated under vacuum.

The ketoester was obtained in the form of a yellow oil.

A mixture of the thus obtained crude product, glacial acetic acid (88 ml) and concentrated H$_2$SO$_4$ (11.7 ml) diluted with 58.6 ml of water, was refluxed for 3 hours.

After cooling down to room temperature and diluting with 351 ml of water, the pH of the solution was adjusted to 6 by adding 10 M KOH and then was extracted with 4 portions each of 220 ml of ether.

The ether extracts were combined, dried, and evaporated under vacuum.

The residue was distilled off whereupon 19.7 g (59.2%) of 3-bromo-5-acetyl-isoxazole in the form of a light yellow colored oil were obtained. The so-obtained product boiled at 75° C./15 mm Hg and on standing crystallized in crystals melting at 56°–58° C. $^1$H NMR (CDCl$_3$): $\delta$6.93 (s, 1H, C=CH—C); $\delta$2.58 (s, 3H, CH$_2$—CO).

EXAMPLE 3

Preparation of 3-bromo-5-bromoacetyl-isoxazole 670 g (2.09 mols) of pyridinium perbromide hydrobromide were added, while stirring, to a solution of 364 g (1.91 mols) of 3-bromo-5-acetyl-isoxazole in 3700 ml of carbon tetrachloride and a stream of dry nitrogen was blown in.

After stirring at room temperature overnight the thus obtained suspension was treated with 500 ml of water.

The organic layer was separated, washed with water, dried, and evaporated under vacuum.

458 g (89%) of 3-bromo-5-bromoacetyl-isoxazole were obtained. The product was in the form of a brown oil, which on standing solidified. The solid, purified by distillation, boiled at 100°–105° C./1.1 mm Hg. $^1$H NMR (CDCl$_3$): $\delta$4.28 (s, 2H, COCH$_2$—Br); $\delta$7.10 (s, 1H, C=CH—C).

EXAMPLE 4

Preparation of the 1-(3-bromo-isoxazol-5-yl)-2-bromoethanol 20.6 g (543 millimols) of NaBH$_3$ were added in portions, while keeping the temperature between 10° and 15° C., to a solution of 113 g (420 millimols) of 3-bromo-5-bromoacetylisoxazole in 2500 ml of methanol kept under stirring.

After stirring for a further 1 hour at 20° C., the solution was acidified by adding 2 N HCl (indicator Congo Red). The methanol was removed under vacuum and the aqueous residue was extracted with 2 portions of 250 ml of ether. The ether extracts were combined, washed with H$_2$O, dried, and evaporated.

110.8 g (97.3%) of 1-(3-bromo-isoxazol-5-yl)-2-bromoethanol were obtained in form of a brown oil which distilled at 165°/0.1 mm Hg. $^1$H NMR (CDCl$_3$): $\delta$6.45 (s, 1H, —C=CH—C—); $\delta$5.10 (t, 1H, —CH(OH)CO); $\delta$3.75; 3.68 (s and d, 2H, —CH$_2$—N).

EXAMPLE 5

Preparation of a 2-(3-bromo-isoxazol-5-yl)-oxirane.

Procedure A

To a suspension of 264 g (110 millimols) of sodium hydride in 100 ml benzene, kept under stirring, there were added dropwise to a solution of 27.10 g (100 millimols) of 1-(3-bromoisoxazol-5-yl)-2-bromoethanol in 50 ml of benzene.

During the addition, the mixture was kept under dry nitrogen and at 20° C. by external cooling. On completion the mixture was continuously stirred at room temperature for 3 hours and then filtered off. The residue was washed with benzene and ether.

The filtrates were combined, washed, and evaporated.

14 g (74%) of 2-(3-bromo-isoxazol-5-yl)-oxirane were obtained in form of a yellow oil. $^1$H NMR (CDCl$_3$): $\delta$6.32 (s, 1H, C=CH—C); $\delta$3.92 (t, 1H, CH—O); $\delta$3.13 (m, 2H, CH$_2$O).

Procedure B

A solution of 63.45 g (932 millimols) of 2-ethinyloxirane in 500 ml of tetrahydrofuran was added dropwise to a solution, stirred and cooled, of ethyl-magnesiumbromide (obtained from 24.3 g of magnesium and 97.2 g of bromoethane) in 500 ml of tetrahydrofuran.

The mixture was heated for 5 minutes at 30°–35° C. and then cooled on an ice-bath.

Dibromoformoxime (80.5 g; 397 millimols) in 300 ml of tetrahydrofuran was added dropwise, and thereafter the mixture was stirred for 2 hours.

The mixture was left to stand overnight at room temperature, and then it was stirred and cooled on an ice-bath. Finally, a cold solution of ammonium acetate (80 g) in 400 ml of water was carefully added dropwise.

The reaction mixture was extracted with ether; the ether extracts were dried and evaporated.

The residue was heated to 90° C. and the unreacted 2-ethinyl-oxirane was distilled off at 85°–88° C.

49 g (65%) of 2-(3-bromo-isoxazol-5-yl)-oxirane were thus obtained.

The data obtained by $^1$H NMR analysis confirmed that the thus-obtained product was identical with the one prepared according to procedure A.

EXAMPLE 6

Preparation of 1-(3-bromo-isoxazol-5-yl)-2-ter.butylaminoethanol

Procedure A 6.03 g (82.5 millimols) of ter.butylamine were added to a solution of 14.25 g (75 millimols) of 2-(3-bromo-isoxazolyl)-oxirane in 160 ml of ethanol, and the mixture was refluxed for 16 hours while stirring.

The solvent was evaporated under vacuum, and the oily residue was partitioned between 50 ml 2 N HCl and 50 ml ether.

The aqueous phase was separated, treated with activated charcoal, and thereafter filtered off.

Powdered sodium carbonate (10 g) was added to the filtrate and the mixture was extracted with ether. The ether extracts were dried and evaporated under vacuum.

12.3 g (62%) of 1-(3-bromo-isoxazol-5-yl)-2-ter.butylaminoethanol were obtained in the form of slightly colored crystals which were recrystallized from isopropyl ether, m.p. 85.5° C.

The elemental analysis gave the following results for $C_9H_{15}O_2N_2Br$:

|  | C | H | N | Br |
| --- | --- | --- | --- | --- |
| found % | 41.24 | 5.76 | 10.63 | 30.34 |
| calculated % | 41.08 | 5.74 | 10.65 | 30.37 |

$^1$H NMR (CDCl$_3$): $\delta$6.33 (s, 1H, C=CH—C); $\delta$4.78 (q, 1H, —CH—O—); $\delta$3.47 (b.s, 1H, OH); $\delta$2.9 (s+d, 2H, CH$_2$); $\delta$1.07 (s, 9H, 3CH$_3$).

Procedure B 12.2 g (167 millimols) of ter.butylamine were added to a solution of 15 g (55.3 millimols) of 1-(3-bromo-isoxazol-5-yl)-2-bromoethanol in 150 ml ethanol, while maintaining the mixture under stirring. The solution was refluxed for 18 hours.

Both the ethanol and ter.butylamine in excess were evaporated; the residue was treated with 50 ml 2 N HCl and extracted with ether.

The aqueous phase was separated and treated as described above under Procedure A.

8 g (55%) of 1-(3-bromo-isoxazol-5-yl)-2-ter.butylaminoethanol were obtained. By crystallization from isopropyl ether, there were obtained 6 g of pure product in the form of colorless crystals; m.p. 85.5° C.

The data obtained from $^1$H NMR analysis confirmed that the thus-obtained product was identical with the one obtained when working according to procedure A.

EXAMPLE 7

Preparation of salts of 1-(3-bromo-isoxazol-5-yl)-2-ter.butylaminoethanol.

By adding the corresponding acids to solutions of the base in suitable solvents, the following salts were obtained:

Hydrochloride: colorless prismatic crystals which began to slowly decompose at 170°–175° C. and that melted at 192°–193° C. (crystallization from acetonitrile).

Elemental analysis for $C_9H_{16}BrClN_2O_2$:

|  | C | H | Cl | N |
| --- | --- | --- | --- | --- |
| found % | 36.04 | 5.37 | 11.78 | 9.23 |
| calculated % | 36.08 | 5.38 | 11.84 | 9.35 |

NMR (D$_2$O): $\delta$6.67 (s, 1H, C—CH—C); $\delta$5.23 (q, 1H, —CH—O—); $\delta$3.40 (s+d, 2H, CH$_2$); $\delta$1.35 (s, 9H, 3CH$_3$).

Sulphate: colorless prismatic crystals; m.p. 213°–215° C. (decomposition) (from methanol).

Elemental analysis for $C_{18}H_{32}Br_2N_4O_8S$:

|  | C | H | N | S | Br |
| --- | --- | --- | --- | --- | --- |
| found % | 34.82 | 5.20 | 9.07 | 5.08 | 25.49 |
| calculated % | 34.63 | 5.17 | 8.97 | 5.13 | 25.60 |

NMR (D$_2$O): The spectrum obtained is identical to that of the hydrochloride.

Maleate (acid): colorless prismatic crystals; m.p. 156°–157° C. (from acetonitrile).

Elemental analysis for $C_{13}H_{19}BrN_2O_6$:

|  | C | H | N | Br |
| --- | --- | --- | --- | --- |
| found % | 41.00 | 5.07 | 7.44 | 20.89 |
| calculated % | 41.17 | 5.05 | 7.39 | 21.07 |

NMR (D$_2$O): $\delta$6.73 (s, 1H, C=CH—C); $\delta$6.30 (s, 2H, —OC—CH=CH—CO—); $\delta$5.27 (q, 1H, —CH—O—); $\delta$3.46 (s+d, 2H, CH$_2$); $\delta$1.42 (s, 9H, 3CH$_3$).

What is claimed is:

1. A pharmaceutical composition for use as a bronchodilator comprising a therapeutically effective amount of a pharmaceutically acceptable salt of 1-(3-bromo-isoxazol-5-yl) - 2 - ter.butylaminoethanol and a pharmaceutically acceptable carrier.

2. 1-(3-bromo-isoxazol-5-yl)-2-ter.butylaminoethanol.

3. Pharmaceutically acceptable salt of 1-(3-bromo-isoxazol-5-yl)-2-ter.butylaminoethanol.

4. A pharmaceutical composition for use as a bronchodilator comprising a therapeutically effective amount of 1-(3-bromo-isoxazol-5-yl)-2-ter.butylaminoethanol and a pharmaceutically acceptable carrier.

* * * * *